United States Patent [19]

Carson

[11] Patent Number: 4,725,602

[45] Date of Patent: Feb. 16, 1988

[54] ACETYLENE AMINES AND THEIR USE AS VASODILATORS AND ANTIHYPERTENSIVES

[75] Inventor: John R. Carson, Norristown, Pa.

[73] Assignee: McNeilab, Inc., Fort Washington, Pa.

[21] Appl. No.: 790,777

[22] Filed: Oct. 24, 1985

Related U.S. Application Data

[63] Continuation of Ser. No. 576,606, Feb. 6, 1984, abandoned.

[51] Int. Cl.⁴ .................. A61K 31/44; A61K 31/38; A61K 31/36; C07D 317/58

[52] U.S. Cl. .................. 514/302; 514/338; 514/347; 514/349; 514/351; 514/412; 514/414; 514/422; 514/424; 514/426; 514/427; 514/443; 514/444; 514/445; 514/447; 514/438; 514/452; 514/465; 514/466; 514/471; 549/495; 549/492; 549/491; 549/480; 549/479; 549/473; 549/443; 549/441; 549/440; 549/435; 549/362; 549/77; 549/75; 549/74; 549/68; 549/62; 549/60; 549/50; 548/561; 548/526; 548/453; 546/337; 546/335; 546/334; 546/329; 546/312; 546/311; 546/304; 546/270; 546/115; 564/382; 564/381; 564/374; 564/361; 564/355; 564/288; 564/287; 564/165; 564/164; 564/162; 560/142; 560/138

[58] Field of Search .......... 549/50, 60, 62, 68, 549/74, 75, 77, 435, 441, 473, 492; 548/526, 561, 453; 546/115, 270, 304, 311, 312, 329, 334, 335, 337; 514/452, 465, 466, 471, 443, 444, 445, 447, 438, 414, 412, 422, 424, 426, 427, 338, 347, 349, 351, 302

[56] References Cited

U.S. PATENT DOCUMENTS

| | | | |
|---|---|---|---|
| 3,719,712 | 3/1973 | Remy | 564/384 |
| 4,128,656 | 12/1978 | Lafon | 549/440 |
| 4,412,856 | 11/1983 | Brunner et al. | 71/121 |

Primary Examiner—Nicky Chan
Attorney, Agent, or Firm—David J. Levy

[57] ABSTRACT

Acetylenes of the following formula (I):

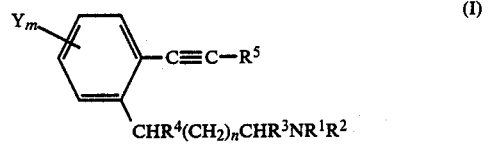

wherein Y, m, $R^1$, $R^2$, $R^3$, n and $R^4$ are defined herein and $R^5$ is hydrogen, alkyl, cycloalkyl or substituted alkyl are useful vasodilators and antihypertensives.

17 Claims, No Drawings

ACETYLENE AMINES AND THEIR USE AS VASODILATORS AND ANTIHYPERTENSIVES

This application is a continuation of application Ser. No. 576,606, filed Feb. 6, 1984, now abandoned.

The present invention comprises various aromatic derivatives of amino acetylenes which are useful as vasodilators and in the treatment of hypertension, e.g. in humans.

Various phenylethynyl benzylamines are claimed in U.S. Pat. No. 3,719,712 and are taught as antiarrhythmic agents.

SUMMARY OF THE INVENTION

Aromatic acetylenes of the following formula (I):

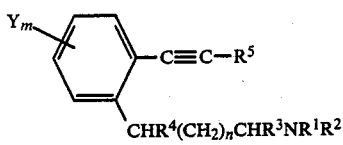

wherein Y, m, $R^1$, $R^2$, $R^3$, n and $R^4$ are as defined herein and $R^5$ is hydrogen, alkyl, cycloalkyl or substituted alkyl possess vasodilating and anti-hypertensive properties when administered to a mammal in need thereof. Also part of the invention are pharmaceutical compositions containing compounds of the formula (I) and methods of treatment using such compositions.

DETAILED DESCRIPTION OF THE INVENTION

Compounds of the invention are of the following formula

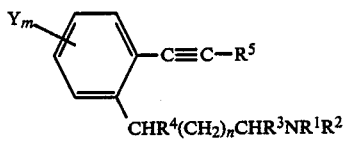

wherein
Y is independently alkyl, alkoxy, alkylthio, alkylsulfinyl, alkylsulfonyl, alkanoyloxy, alkanoylamino, amino, monoalkylamino, dialkylamino, hydroxy, halogen or cyano or methylenedioxy or ethylenedioxy at adjacent ring carbons;
m is 0, 1, 2 or 3;
$R^1$ and $R^2$ are independently hydrogen, alkyl

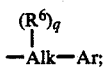

$R^3$ is hydrogen, alkyl or alkoxyalkyl
n is 0, 1 or 2;
$R^4$ is hydrogen or alkyl;
$R^5$ is hydrogen, alkyl, cycloalkyl or alkyl substituted by amino, monoalkylamino, dialkylamino, hydroxy, cycloalkyl, alkoxy, phenyl or phenyl substituted by 1 to 3 Y groups;
Alk is a straight chain alkylene of about 1 to 4 carbons;
Ar is a phenyl, phenoxy, thiophenoxy or a 5- or 6-membered heterocyclic aromatic ring which rings may be substituted independently by one or more of alkyl, alkoxy, alkylthio, hydroxy, halogen, fluoroalkyl, amino or dialkylamino or by methylenedioxy at adjacent ring carbons;
$R^6$ is alkyl; and
q is 0, 1 or 2 or 3 if Alk is alkylene of about 2 to 4 carbons,
and the pharmaceutically acceptable acid addition salts and quarternary ammonium compounds thereof.

In particular, Y is alkyl of about 1 to 6 carbons such as methyl or ethyl; alkoxy of about 1 to 6 carbon atoms such as methoxy or ethoxy; alkylthio of about 1 to 6 carbons such as methylthio; alkylsulfinyl of about 1 to 6 carbons such as methylsulfinyl; alkylsulfonyl of about 1 to 6 carbons such as methylsulfonyl; alkanoyloxy of about 2 to 6 carbons such as acetoxy; alkanoylamino of about 2 to 6 carbons such as acetylamino; amino; monoalkylamino of about 1 to 6 carbons such as ethylamino; dialkylamino of about 2 to 12 carbons such as dimethylamino; hydroxy; halogen such as fluoro, chloro or bromo; cyano; or methylenedioxy or ethylenedioxy wherein the two oxygen atoms are attached to two adjacent carbons of the benzene ring. Although the Y groups may be attached at any of the 4 open positions of the benzene ring, particularly preferred are compounds wherein the Y groups are attached at the 4- and/or 5-positions of the ring relative to the amino side chain with the acetylene moiety being at the 2-position.

$R^1$ and $R^2$ are independently hydrogen; alkyl of about 1 to 8 carbons, e.g., 1 to 4 carbons such as methyl, ethyl, n-Propyl, iso-propyl, tert-butyl or n-hexyl; or $$\begin{matrix} (R^6)_q \\ | \\ -Alk-Ar \end{matrix}$$

$R^3$ is hydrogen; alkyl of about 1 to 6 carbons such as methyl, ethyl, iso-propyl and n-pentyl; or alkoxyalkyl of about 1 to 6 carbons in each alkyl portion such as methoxymethyl, n-butoxymethyl and ethoxyethyl.

$R^4$ is in particular, hydrogen; or alkyl of about 1 to 6 carbons with examples being methyl, ethyl and n-butyl.

$R^5$ is in particular hydrogen; alkyl of about 1 to 12 carbons, e.g., about 1 to 8 carbons, such as methyl, ethyl, n-butyl, iso-butyl, sec-butyl, tert-butyl, n-hexyl or n-octyl; cycloalkyl of about 5 to 7 carbons such as cyclopentyl, cyclohexyl and cycloheptyl; or an alkyl of about 1 to 6 carbons, such as methyl, ethyl, n-propyl, or iso-propyl, substituted by an amino, monoalkylamino of about 1 to 6 carbons, dialkylamino of about 2 to 12 carbons, hydroxy, cycloalkyl of about 5 to 7 carbons, e.g., cyclopentyl, cyclohexyl or cycloheptyl, alkoxy of about 1 to 6 carbons such as methoxy or ethoxy, phenyl or phenyl substituted by 1, 2 or 3 Y groups such as methyl, methoxy, fluoro, chloro or cyano. Alkyl groups for the mono- and di-alkylamino include methyl, ethyl and n-propyl, particular examples being the dialkylamino groups wherein the alkyl groups are the same.

Alk is methylene, ethylene, trimethylene or tetramethylene.

Ar in particular is phenyl; phenoxy; thiophenoxy; or a 5- or 6-membered heterocyclic aromatic ring, preferably one having 1 heteroatom such as nitrogen, sulfur or oxygen, e.g. furan or thiophene attached at the 2 or 3 position, pyrrole attached at the 1, 2 or 3 position and pyridine attached at the 2, 3 or 4 position. The open positions of the ring of Ar may be substituted by one or more, e.g. one or two, same or different, of alkyl of about 1 to 6 carbons such as methyl or ethyl; alkoxy of about 1 to 6 carbons such as methoxy and ethoxy; alkylthio of about 1 to 6 carbons such as methylthio; hydroxy; halogen such as fluoro, chloro and bromo; fluoroalkyl of about 1 to 6 carbons and one or more fluorine atoms with examples being 2,2,2-trifluoroethyl and trifluoromethyl; amino; or dialkylamino of about 2 to 12 carbons such as dimethylamino; or methylenedioxy at adjacent ring carbons particularly if Ar is phenyl, phenoxy or thiophenoxy, e.g., 3,4-methylenedioxyphenyl.

$R^6$ is alkyl of about 1 to 4 carbons such as methyl, ethyl or iso-propyl.

q is 0, 1 or 2 or 3 if Alk is alkylene of about 2 to 4 carbons, and in particular is 0, 1 or 2.

"Alkyl" in the present specification, e.g., as part of an alkoxy group, is meant to include straight and branched chain alkyl.

The pharmaceutically acceptable acid-addition salts of the compounds of formula (I) include those of a mineral or organic acid such as hydrochloric, hydrobromic, hydroiodic, sulfuric, phosphoric, fumaric, maleic, cyclohexylsulfamic, citric, lactic, methanesulfonic and similar acids.

The quaternary ammonium compounds of the compounds of formula (I) include those formed with an alkylhalide or sulfate of about 1 to 6 carbons, e.g., an alkyl bromide or iodide such as methyl iodide. The salts and ammonium compounds may be prepared by conventional techniques.

Compounds of Formula (I) and other compounds of the invention may exist in various isomeric forms, e.g., in view of the presence of an asymmetric carbon. It is understood that the present invention includes all such individual isomers and their racemates. Also within the scope of the invention are compounds of the invention in the form of hydrates and other solvate forms.

Particularly preferred aspects of the present invention are compounds of formula (I) wherein:

A. Y is alkoxy and m is 1 or 2.
B. Y is alkoxy and m is 1 at the position para to acetylene moiety or Y is alkoxy and m is 2 at positions para to the acetylene moiety and to the $-CHR^4(CH_2)_n-CHR^3NR^1R^2$ moiety.
C. one of $R^1$ and $R^2$ is hydrogen or alkyl.
D. $R^1$ and $R^2$ are both alkyl or $R^1$ is alkyl and $R^2$ is 2-(3,4-dimethoxyphenyl)ethyl.
E. $R^5$ is hydrogen, alkyl, cycloalkyl or alkyl substituted by dialkylamino, hydroxy or phenyl.
F. $R^1$ is alkyl and $R^2$ is

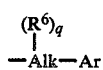
—Alk—Ar wherein Alk is ethylene and q is 0.
G. Y is alkoxy, alkylthio, amino, halogen or methylenedioxy at adjacent ring carbons; m is 0, 1 or 2; $R^1$ and $R^2$ are independently alkyl or

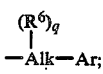
—Alk—Ar;

$R^3$ is hydrogen or alkyl; n is 0 or 1; $R^4$ is hydrogen; $R^5$ is hydrogen, alkyl, cycloalkyl or alkyl substituted by dialkylamino, hydroxy or phenyl; and Ar is phenyl substituted by one or more alkoxy groups.

Particular compounds of the invention of the formula (I) are the following:

2-(1-Hexynyl)-5-methoxy-N,N-dimethylbenzeneethanamine
2-(Cyclohexylethynyl)-3,4-dimethoxy-N,N-dimethylbenzeneethanamine
2-(1-Hexynyl)-5-methoxy-N,N-dimethylbenzenepropanamine
N-[2-(3,4-Dimethoxyphenyl)ethyl]-6-(1-hexynyl)-N-methyl-1,3-benzodioxole-5-propanamine
2-(1-Decynyl)-5-methoxy-N,N-dimethylbenzenepropanamine
2-(3,3-Dimethylbutynyl)-5-methoxy-N,N-dimethylbenzenepropanamine
N-[2-(3,4-Dimethoxyphenyl)ethyl]-2-(1-hexynyl)-5-methoxy-N-methylbenzenepropanamine
N-[2-(3,4-Dimethoxyphenyl)ethyl]-2-(3,3-dimethylbutynyl)-5-methoxy-N-methylbenzenepropanamine
N-[2-(3,4-Dimethoxyphenyl)ethyl]-5-methoxy-N-methyl-2-(4-phenyl-1-butynyl)benzenepropanamine
2-[3-(Diethylamine)-1-propynyl]-N-[2-(3,4-dimethoxyphenyl)ethyl]-5-methoxy-N-methylbenzenepropanamine
2-(Butynyl)-N-[2-(3,4-dimethoxyphenyl)ethyl]-5-methoxy-N-methylbenzenepropanamine
2-(Cyclohexylethynyl)-N-[2-(3,4-dimethoxyphenyl)ethyl]-5-methoxy-N-methylbenzenepropanamine
2-(1-Hexynyl)-5-methoxy-N,N-dimethylalphapentyl-benzenepropanamine
2-(Cyclohexylethynyl)-N-[2-(3,4-dimethoxyphenyl)ethyl]-5-methoxy-N,alphadimethylbenzeneethanamine
N-[2-(3,4-Dimethoxyphenyl)ethyl]-2-(1-hexynyl)-5-methoxy-N,alphadimethylbenzeneethanamine
N-[2-(3,4-Dimethoxyphenyl)ethyl]-2-(3-hydroxy-3-methylbutynyl)-5-methoxy-N-methylbenzenepropanamine
N-[2-(3,4-Dimethoxyphenyl)ethyl]-2-ethynyl-5-methoxy-N-methylbenzene-propanamine
N-[2-(3,4-Dimethoxyphenyl)ethyl]-2-(1-hexynyl)-5-methoxy-N-methyl-α-pentyl-benzenepropanamine.

Compounds of formula (I) may be prepared according to the following Reaction Scheme I:

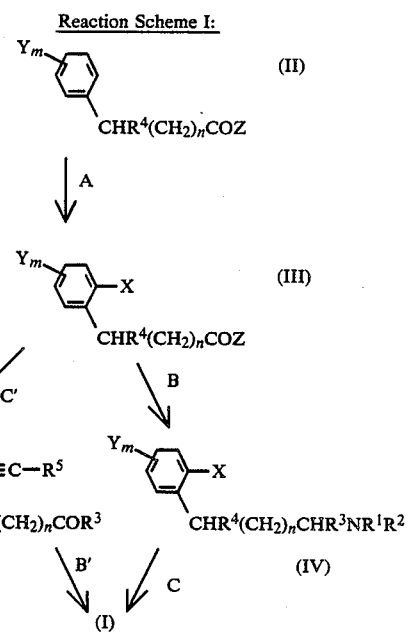

Three primary stages are used in the preparation of compounds of the formula (I) by starting with arylalkanoic acids or arylalkanones of the formula (II) wherein Z is OH, O-alkyl or $R^3$, e.g., hydrogen, alkyl or alkoxyalkyl. The stages are halogenation, construction of an amine functionality and condensation with an $R^5$-acetylene. In the halogenation stage A, wherein X is a halogen such as Br or I, the aryl ring of (II) is halogenated in the position ortho to the eventual aminoalkyl side chain. Brominations may be carried out with bromine in halocarbon solvents or acetic acid at temperatures from about −20° to 80° C. and may be conducted in the presence of a Lewis acid catalyst such as ferric chloride. Iodinations may be carried out using iodine monochloride in halocarbon solvents or acetic acid over a range of room temperature to about 100° C. Iodinations may be carried out using iodine in the presence of an iodine scavenger such as silver acetate, silver sulfate, mercuric oxide or nitric acid. For reactive substrates, iodine may be used alone or in conjunction with a mild base such as sodium bicarbonate. Alternatively, the halogenation may be accomplished by mercuration, e.g., with $HgCl_2$ or thallation, e.g., with $Tl(O_2CCF_3)_3$, followed by treatment with iodide or bromide as described by A. McKillop, et al. in J. Am. Chem. Soc., 93, 4841 (1971).

In stage B or B' the desired amine function is constructed. In a first embodiment for Stage B and if $R^3$ is to be hydrogen, a compound of formula (III) wherein Z is OH may be converted to the corresponding acid chloride by reagents such as oxalyl chloride, thionyl chloride or phosphoryl chloride. The reaction may be carried out at room temperature to about 100° C. in an aprotic, nonpolar solvent such as toluene, chloroform or methylene chloride or the reaction may be carried out neat. The preferred method employs oxalyl chloride in toluene in the presence of DMF. The acid chloride is converted to the corresponding amide of formula (III) wherein Z is $NR^1R^2$. This conversion may be carried out by treatment of the acid chloride with an excess of amine of the formula $R^1R^2NH$, for instance in toluene or a halocarbon solvent at temperatures from −30° C. to 45° C. Alternatively, slightly more than one equivalent of amine may be used in the presence of an auxillary base such as triethylamine, pyridine, sodium hydroxide or potassium carbonate. The amide is then reduced to the corresponding amine of the formula (IV) wherein $R^3$ is hydrogen to complete elaboration of the amine function. The reduction of the amide is preferably carried out with an excess of borane in THF at the reflux temperature of the solvent. The excess borane is decomposed by addition of water and the amine borane complex is decomposed by heating in the presence of an alkanoic acid, preferably propionic acid, a mineral acid or an alkali metal hydroxide to give the amine of formula (IV) wherein $R^3$ is hydrogen. Alternatively, the amide may be reduced with lithium aluminum hydride, sodium borohydride plus aluminum chloride or sodium borohydride in acetic or trifluoroacetic acid. A second embodiment for the construction of the amine function consists of reductive alkylation by aldehydes or ketones of the formulae (III) or (V) wherein Z is $R^3$, i.e., hydrogen, alkyl or alkoxyalkyl, of amines of the formula $NHR^1R^2$. The reductive alkylation may be carried out in one step from the carbonyl compound and the amine using sodium cyanoborohydride as the reducing agent in a lower alkanol or acetonitrile as the solvent at neutral to mildly acidic pH at temperatures from 0° to 40° C. Hydrogenation over a noble metal catalyst may also be used to bring about the reduction. Reductive alkylation may also be carried out in two steps. The carbonyl compound and amine are first converted to an imine or iminium salt by treatment with molecular sieves or azeotropic removal of water. Reduction is then effected by sodium cyanoborohydride or catalytic reduction. Using the two step reductive alkylation, the alkyl groups $R^1$ and $R^2$ may be attached sequentially. In stage B', the reductive alkylation cannot be carried out by catalytic hydrogenation in view of the possibility of hydrogenation of the acetylene moiety.

If $R^1$ is to be methyl, the Eschweiler-Clark procedure using formaldehyde as the carbonyl compound and formic acid or sodium cyanoborohydride as the reducing agent is used.

The third stage in Reaction Scheme I is the replacement of halide X by an $R^5$-acetylene and is labeled C and C'. The coupling of the arylhalides (III) or (IV) with an $R^5$-acetylene may be accomplished by treating the arylhalide with chlorozinc $R^5$-acetylide in the presence of a palladium or nickel catalyst, preferably $Pd[(Ph_3)P]_4$ in an ethereal solvent such as THF at −30° C. to ambient temperature, as described by A. O. King et al. in J. Org. Chem., 43, 358 (1978). The coupling may also be accomplished by treating the arylhalide (III) or (IV) with the $R^5$-acetylene and catalytic quantities, e.g., 0.5 to 10 mole percent, of $Pd(OAc)_2[P(Ph)_3]_2$ or $PdCl_2[P(Ph)_3]_2$ in an amine solvent such as diethylamine, piperidine, pyrrolidine or triethylamine at ambient temperature to the reflux temperature of the solvent in the presence or absence of cuprous iodide as described by K. Sonogashira et al. in Tetrahedron Letters, 4467 (1975) or H. A. Dieck et al. in J. Organometal. Chem. 93, 253 (1975).

For the preparation of the compounds of formula (I) wherein $R^5$ is hydrogen, the corresponding compound wherein $R^5$ is 1-hydroxy-1-methylethyl may be treated with base. For example, the compound of formula (I) wherein $R^5$ is 1-hydroxy-1-methylethyl may be heated at 50°–140° C. in an inert solvent such as toluene, xylene or chloroform in the presence of concentrated aqueous sodium hydroxide in the presence of a quaternary ammonium phase transfer catalyst such as, for example, tetrabutylammonium chloride.

The stages of reaction Scheme I may be carried out in the sequence A, B and C or the sequence A, C' and B'. When $R^1$ is to be alkyl, such may be attached by reductive alkylation after carrying out stage C or B'. If desired, the order in which the stages are carried out may be varied so tht amine elaboration may preceed halogenation.

A second general method for preparation of compounds of formula (I) where n is 0 $R^4$ is H and $R^3$ is alkyl is shown in Reaction Scheme II:

Reaction Scheme II

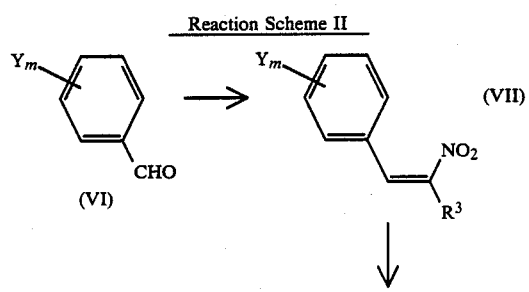

-continued
Reaction Scheme II

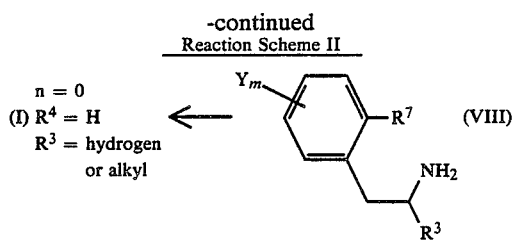

n = 0
(I) $R^4 = H$
$R^3$ = hydrogen or alkyl

An aromatic aldehyde (VI) is condensed with a nitroalkane of the formula $R^3CH_2NO_2$ to afford a nitroolefin (VII). Condensation of the nitroalkane with the aromatic aldehyde is carried out using ammonium acetate or a primary alkylamine as catalyst in, for example, glacial acetic acid, ethanol or toluene as the solvent at ambient to elevated temperatures preferably at the reflux temperature of the solvent. The nitroolefin (VII)

metal hydroxide followed by thermal decarboxylation affords the arylalkanone (II) wherein Z is $R^3$, n is O and $R^4$ is hydrogen. Conversion of such a (II) compound to one wherein $R^4$ is alkyl may be carried out by alkylation of an alkali metal enolate of the carbonyl compound (II) with a reagent such as ethyl iodide.

Second, arylalkanones of the formula (II) where Z is $R^3$, n is 1 and $R^4$ is hydrogen may be prepared by a Claisen-Schmidt condensation of a methyl ketone, $CH_3COR^3$ with an aromatic aldehyde (VI) in the presence of an alkali metal hydroxide followed by hydrogenation of the alpha,beta-unsaturated ketone (X) over a noble metal catalyst. Third, arylalkanoic acids of the formula (II) wherein Z is OH, $R^4$ is hydrogen and n is 1 may be prepared by Knoevenagel condensation of an aromatic aldehyde (VI) with malonic acid followed by hydrogenation of the resulting cinnamic acid (XI) over a noble metal catalyst:

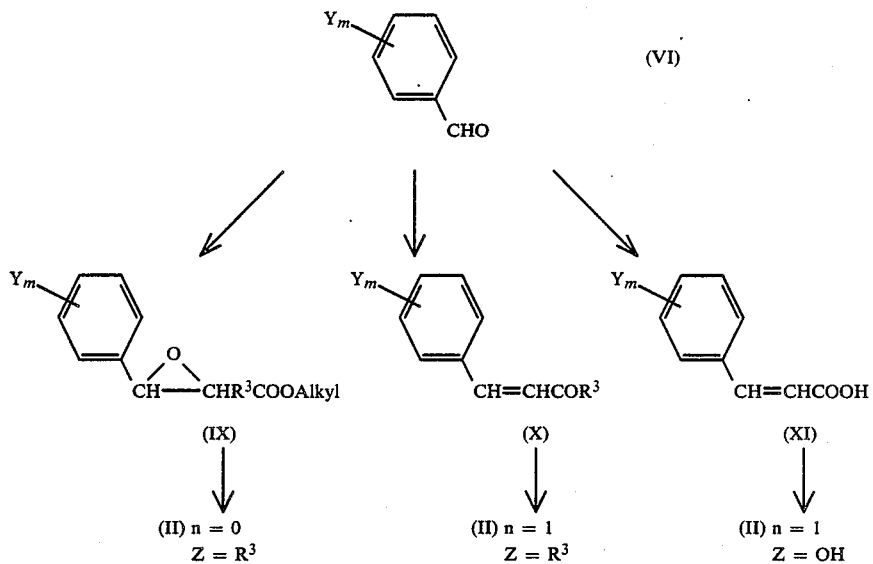

is then reduced to an amine (VIII) where $R^7$ is hydrogen with lithium aluminum hydride in an ether solvent, or by catalytic reduction over Raney nickel or a noble metal catalyst. The amine (VIII) is halogenated on the aromatic ring using the methods described for Stage A to afford a halogenated amine of the formula (VIII) where $R^7$ is halo. The haloamine is coupled with an $R^5$-acetylene using the procedure of King et al. or Sonogashiri et al. as described for Stage C to give an acetylene of formula (VIII) where $R^7$ is $-C\equiv C-R^5$. Attachment of the groups $R^1$ and/or $R^2$ by reductive alkylation starting with the appropriate carbonyl compounds, e.g., $CH_3CHO$ to have ethyl as the $R^1$ moiety or benzaldehyde to give benzyl as the -Alk-Ar moiety, affords the product of the formula (I) wherein n is 0 $R^4$ is hydrogen and $R^3$ is hydrogen or alkyl.

Starting materials for Reaction Schemes I and II are widely known. However, starting materials with particular substituents may be synthesized by the following methods:

First, alkanones of the formula (II) wherein Z is $R^3$, n is 0 and $R^4$ is hydrogen may be prepared by condensation of an aromatic aldehyde (VI) with an alpha-halo-ester, e.g. of the formula $R^3CHBrCOOAlkyl$ in the presence of an alkali metal alkoxide to give a glycidic ester of the formula (IX). Hydrolysis with an alkali In each of the above three sequences, the aromatic aldehyde may be one with an X group ortho to the CHO and such a starting material will result in final products of the formula (III) after the steps described above.

For the preparation of intermediates (II) and (III) where Y is halo, alkylthio, hydroxy, cyano or dialkylamino, the corresponding compounds (XII) where p is 0 or 1, respectively, may be utilized as starting materials. The arylamine (XII) may be diazotized to give (XIII) and the diazonium group may be treated with CuCl, CuBr or CuCN to yield (II) or (III) wherein Y is Cl, Br or CN, respectively. Pyrolysis of the diazonium fluoroborate or hexafluoro phosphate gives the corresponding aryl fluoride. Hydrolysis of the diazonium salt would lead to the corresponding phenol. Treatment of the diazonium salt successively with potassium ethyl xanthate, base and an alkyl halide leads to the alkylthio product. Reductive alkylation of the amino compound (XII) with formaldehyde or an alkanal and sodium cyanoborohydride gives rise to intermediates (II) or (III) bearing the dialkylamino group.

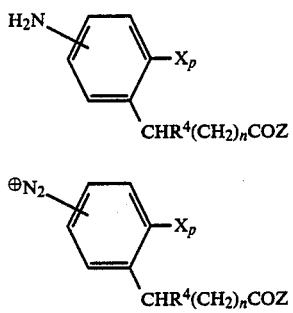

The various Y groups in compounds such as those of formulae (II), (III), (IV) and (XII) may be transformed among each other by techniques known in the art. For example, when Y is amino, the corresponding compound wherein Y is monoalkylamino may be prepared by acylation with an acyl halide or anhydride to yield the corresponding compound where Y is alkanoylamino followed by hydride reduction with borane or lithium aluminum hydride. When Y is alkylthio the corresponding compound where Y is alkylsulfinyl or alkylsulfonyl may be produced by oxidation with hydrogen peroxide or a peracid such as trifluoroperacetic acid known in the art. Variation in the reaction temperature, reaction time and reactivity of the substrate and the particular reagent will all be factors influencing whether the product is the sulfinyl or sulfonyl and manipulation of such variables is well known in the art. When Y is alkoxy, the corresponding compound wherein Y is hydroxy may be produced by conventional dealkylating reagents such as boron tribromide, boron trichloride, trimethylsilyliodide and hydrogen iodide. The thus-produced amino compound may be iodinated at the 2-position to yield a compound of formula (III) and then the Y group may be transformed into an alkylthio group by reaction with sodium nitrate, potassium ethyl xanthate and an alkyliodide or into a fluoro group by reaction with hexafluorophosphoric acid in hydrochloric acid. In addition, compounds wherein Y is alkoxy may be produced from the phenol by alkylation with a reagent such as alkyl halide, e.g., methyl iodide, in the presence of a base.

$R^5$-acetylenes used in Stage C or C' may be obtained from Farchan Laboratories of 4702 East 355th Street, Willoughby, Ohio 44094. Alternatively, the terminal $R^5$-acetylenes may be prepared by alkylation of metalloacetylenes as described by G. H. Viehe in "Chemistry of the Acetylenes", Marcel Dekker, New York (1969) page 170.

Compounds of the formula (I), including the acid-addition salts and quaternary compounds thereof, are calcium blockers and as such, are effective against angina, hypertension and cardiac arrhythmias in mammals, particularly as described by S. F. Flaim et al. in "Calcium Blockers—Mechanisms of Action and Clinical Applications", Urban and Schwarzenberg, Baltimore, Md. (1982). Techniques used to determine efficacy as a calcium blocker are described by S. F. Flaim et al. in Pharmacology, Vol. 22, p. 286 to 293 (1981). Compounds of the invention have the advantage of a significant separation between the desirable coronary vasodilator effects and the less desirable side effect of decreased myocardial contractile force.

The activity of compounds of formula (I) for the treatment of hypertension was determined using the Spontaneously Hypertensive Rat (SHR) test as described below.

In this test, the arterial pressure of adult spontaneously hypertensive rats (Charles River) is monitored directly via an aortic cannula. The SH rats are anesthetized with an inhalation anesthetic (ether). The left carotid artery is isolated and cannulated. The tip of the cannula is advanced to the aorta and the cannula is exteriorized behind the neck at the level of the scapula. Animals are placed in individual cages and allowed to recover from the anesthetic and are kept unrestrained. The arterial cannula is connected to the pressure transducer which is attached to the recorder. The test compounds are administered to at least 3 rats at doses selected in the range of 0.1 to 100 mg/kg of body weight by intraperitoneal (i.p.) or oral (p.o.) routes of administration. The arterial pressure and heart rate are monitored for a minimum of 24 hours. A test compound is considered to be active as an antihypertensive agent if the mean arterial pressure (MAP) indicates a fall of >15 mm of Hg. Each animal serves as its own control.

In addition to their utility in the treatment of hypertension, the compounds of formula (I) are useful in the treatment of the symptoms of angina pectoris by virtue of their ability to dilate coronary arteries. Their activity was measured using the "Langendorff's isolated heart" preparation. This test has been described in "Pharmacological Experiments on Isolated Preparations", Staff of the Department of Pharmacology, University of Edinbourgh, 2nd Ed., Churchill Livingstone, N.Y., 1970, pp. 112-119. The test compounds were adminsistered at concentrations of 30.0, 10.0, 3.0, 1.0, 0.3, 0.1, 0.03, and 0.01 micromolar ($10^{-6}$ molar).

The utility of compounds of the invention is demonstrated by results obtained in the above tests for compounds of formula (I) wherein $R^1=CH_3$; $R^2=Alk(R^6)q$ Ar; $Alk=-CH_2CH_2$; $q=O$; $Ar=3,4$-dimethoxyphenyl; and $R^4=H$ in the following Table I:

| Compound Example | Y | n | $R^3$ | $R^5$ | SHR Max fall bp[d] (dose)[e] | Langendorff $EC_{30}$ ($10^{-6}$ M) |
|---|---|---|---|---|---|---|
| 20 | 5-OCH$_3$[a] | 1 | H | n-C$_4$H$_9$ | −35(30) | 0.1 |
| 29 | 5-OCH$_3$[b] | 1 | n-C$_5$H$_{11}$ | n-C$_4$H$_9$ | −36(30) | 0.03 |
| 20 | 4,5-(OCH$_2$O)[c] | 1 | H | n-C$_4$H$_9$ | −30(100) | 0.3 |
| 22 | 5-OCH$_3$ | 0 | CH$_3$ | cyclohexyl | −65(10) | 0.03 |

[a]administered as the cyclohexylsulfamate
[b]administered as the oxalate
[c]administered as the free base
[d]in mm of Hg
[e]in mg/kg of body weight per os For the treatment of hypertension or angina, compounds of the present invention of the formula (I) may be administered orally or parenterally in a pharmaceutical composition comprising about 1 to 2,000 mg, preferably about 30 to 400 mg of one or more of the acetylene compounds per day for an average adult human depending on the activity of the particular compound chosen. The dosage may be divided into 1 to 4 unit dosage forms per day. While the therapeutic methods of the invention are most useful for human subjects in need of alleviation of hypertension or angina, the compounds may be administered to other mammals at comparable dosages per weight of the subject.

Pharmaceutical compositions containing the acetylene compounds of the present invention of formula (I), an acid addition salt thereof or a quaternary ammonium compound thereof as the active ingredient may be prepared by intimately mixing the acetylene compound with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, including liquid carriers such as water, glycols, oils, alcohols and the like for oral liquid preparations such as suspensions, elixers and solutions; and solid carriers such as starches, sugars, kaolin, calcium stearate, ethyl cellulose, etc., including materials which function as lubricants, binders, disintegrating agents and the like for powders, capsules and tablets. Because of their ease in administration, tablets and capsules represent the most advantageous oral dosage form. These compositions employ solid pharmaceutical carriers such as the aforementioned starches, sugars, kaolin and the like, generally with a lubricant such as calcium stearate. It is especially advantageous to formulate the aforementioned pharmaceutical compositions in dosage unit form for ease of administration and uniformity of dosage. The term "dosage unit form" as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets, capsules, pills, powder packets, wafers, teaspoonful, tablespoonful and the like, and segregated multiples thereof.

In the following Examples, the following abbreviations are used: E (trans); Z (cis); bp (boiling point); mp (melting point); g (grams); ml (milliliters); glc (gas liquid chromatography); NMR (nuclear magnetic resonance); J (coupling constant); d (doublet); dd (doublet of doublets); s (singlet); m (multiplet); t (triplet); N (normal); M (molar); THF (tetrahydrofuran); MeOH (methanol); DMF (dimethylforamide); mmoles (millimoles); mg (milligrams); mm (millimeters); and C,H,N, etc. (the chemical symbols for the elements). Unless otherwise indicated, all temperatures are reported in degrees centigrade (°C.) and all pressures in mm of mercury.

EXAMPLE 1

2-Iodo-5-methoxybenzeneacetic Acid

A solution of 45 g (0.27 mole) of 3-methoxybenzeneacetic acid, 52.6 g (0.32 mole) of iodine monochloride and 1 g of iodine was allowed to stand in 500 ml of glacial acetic acid for six days at room temperature. The reaction was poured into water and the solid collected. It was recrystallized from toluene to give 51 g of crystalline 2-iodo-5-methoxybenzeneacetic acid, mp 133.5°–134.5° C. (65% yield).

EXAMPLE 2

Using the procedure of Example 1 and employing equivalent quantities of the following benzenealkanoic acids in place of 3-methoxybenzeneacetic acid, the following o-iodobenzenealkanoic acids were obtained respectively as products:

| Starting Acid | Product | % Yield | mp (°C.) |
|---|---|---|---|
| 3,4-Dimethoxybenzeneacetic Acid | 4,5-Dimethoxy-2-iodobenzeneacetic Acid | 82 | 165–7 |
| 3-Methoxybenzenepropanoic Acid | 2-Iodo-5-methoxybenzenepropanoic Acid | 69 | 98–101 |
| 3,4-Dimethoxybenzenepropanoic Acid | 4,5-Dimethoxy-2-iodobenzenepropanoic Acid | 88 | 149–151 |
| 3,5-Dimethoxybenzenepropanoic Acid | 3,5-Dimethoxy-2-iodobenzenepropanoic Acid | | |
| 1,3-benzodioxole-5-propanoic acid | 6-Iodo-1,3 benzodioxole-5-propanoic Acid | 66 | 143–5 |

EXAMPLE 3

2-Iodo-5-methoxybenzenepropanoic Acid

Samples of iodine (138.6 g, 0.759 mole) and silver acetate (126.7 g, 0.759 mole) were added in portions over 20 min to a solution of 138.6 g (0.759 mole) of 3-methoxybenzenepropanoic acid in 750 ml glacial acetic acid. An additional 250 ml of glacial acetic acid was added. The mixture became warm and was stirred for one hour. The precipitated silver iodide was filtered and washed with acetic acid and the iltrate was poured into ice water and the solid collected. The solid was taken up in eiother, washed with sodium thiosulfate solution and brine, dried with MgSO$_4$ and the solvent evaporated in vacuo. The residue was recrystallized from CHCl$_3$/ligroin to give 148.7 (64% yield) of 2-iodo-5-methoxybenzenepropanoic acid, mp 105°–106° C.

EXAMPLE 4

1-(2-Iodo-5-methoxyphenyl)butane-3-one

Samples of iodine (42.4 g, 0.167 mole) and silver acetate (27.87 g, 0.167 mole) were added in portions to a solution of 29.8 g (0.167 mole) of 1-(3-methoxyphenyl)butane-3-one in 167 ml of glacial acetic acid. The mixture was stirred one hour. The silver iodide was removed by filtration and washed with acetic acid. The filtrate was partitioned between ether and water. The ether layer was washed with water, sodium bicarbonate solution and sodium thiosulfate solution. The ether solution was dried with MgSO$_4$ and evaporated to dryness in vacuo. There was obtained 41.8 g (82% yield) of oily 1-(2-iodo-5-methoxyphenyl)butane-3-one.

$^1$HNMR (CDCl$_3$): 7.5–7.8 (d, J=9, 1H); 6.75–6.9 (d, J=3, 1H); 6.3–6.65 (dd, J=3, 10, 1 H); 3.7–4.0 (s, 3H); 2.5–3.1 (m, 4H); 2.2 (s, 3H).

EXAMPLE 5

Using the procedure of Example 4 and substituting the appropriate ketone for 1-(3-methoxyphenyl)butane-3-one the following products were obtained respectively:

(2-iodo-5-methoxyphenyl)-2-propanone, mp 57°–58°
1-(2-iodo-5-methoxy-phenyl)octan-3-one

EXAMPLE 6

N,N-Dimethyl-2-iodo-5-methoxybenzeneacetamide

A 16.7 g (0.19 mole) sample of oxalyl chloride was added dropwise at 0° C. to a solution of 50.0 g (0.17 mole) of 2-iodo-5-methoxybenzeneacetic acid in 310 ml dry toluene and 31.7 ml of DMF. The mixture was allowed to warm to room temperature and stir for 16 hours. The solution was cooled to 0° C. and dimethylamine gas was admitted until the mixture was strongly basic. The mixture was allowed to warm to room temperature and stir for three hours and methylene chloride was added. The organic layer was washed with water, dilute hydrochloric acid, and sodium hydroxide. The organic layer was dried with MgSO$_4$ and evaporated in vacuo to give 54.2 g of N,N-dimethyl-2-iodo-5-methoxybenzeneacetamide, mp 86°–89° C.
Elemental Analysis: Calculated for $C_{11}H_{14}INO_2$: C, 41.39; H, 4.42; Found: C, 41.43; H, 4.45.

EXAMPLE 7

2-Iodo-5-methoxybenzenepropanoyl chloride

To a solution of 13.0 g (0.042 mole) of 2-iodo-5-methoxybenzenepropanoic acid and 4 ml of DMF in 80 ml of dry toluene at 0° C. was added 4.00 ml (0.046 mole) of oxalyl chloride over 15 min. The reaction was stirred overnight to give a solution 2-iodo-5-methoxybenzenepropanoyl chloride in toluene.

EXAMPLE 8

Following the procedure of Example 7 and employing equivalent quantities of the appropriate iodoarylalkanoic acid in place of 3-methoxybenzenepropanoic acid there were obtained as products, respectively:
3,4-Dimethoxy-2-iodobenzenacetyl chloride
1,3-Benzodioxole-2-iodo-5-propanoyl chloride
2-Iodo-5-methylthiobenzenepropanoyl chloride
2-Iodo-5-fluorobenzenepropanoyl choride

EXAMPLE 9

N-[2-(3,4-Dimethoxyphenyl)ethyl]-2-iodo-5-methoxy-N-methylbenzenepropanamide

A solution of 13.8 g (0.042 mole) of 2-iodo-5-methoxybenzenepropanoyl chloride in 80 ml of toluene was cooled to 0° C. and 24.6 g (0.126 mole) of N-methylhomoveratrylamine was added over a 15-minute period. An additional 50 ml of toluene was added. The temperature was allowed to warm to room temperature and stirring continued for 3½ hours. The mixture was partitioned between 500 ml of methylene chloride and 400 ml of water. The methylene chloride layer was separated and washed with 400 ml of 5% hydrochloric acid followed by a washing with 400 ml of 5% sodium hydroxide solution. The organic phase was dried over anhydrous magnesium sulfate and evaporated in vacuo to yield N-[2-(3,4-dimethoxyphenyl)ethyl]-2-iodo-5-methoxy-N-methylbenzenepropanamide, a pale yellow oil that partially crystallized on standing.

EXAMPLE 10

Following the procedure of Example 9 and employing an equivalent quantity of the appropriate arylalkanoyl halide in place of 2-iodo-5-methoxybenzenepropanoyl chloride and an equivalent quantity of the appropriate amine for N-methylhomoveratrylamine the following amides were added obtained as products, respectively:

| Product | mp °C. |
| --- | --- |
| 2-Iodo-4,5-dimethoxy-N,N—dimethylbenzeneacetamide | 101–103 |
| N—[2-(3,4-Dimethoxyphenyl)ethyl]-2-iodo-N—methyl-5-methylthiobenzenepropanamide | oil |
| N—[2-(3,4-Dimethoxyphenyl)ethyl]-6-iodo-N—methyl-1,3-benzodioxole-5-propanamide | oil |
| N—[2-(3,4-Dimethoxyphenyl)ethyl]-2-iodo-5-methoxy-N—methylbenzenepropanamide | 105–106 |
| 2-Iodo-5-methoxy-N,N—dimethylbenzenepropanamide | oil |
| N—[2-(3,4-Dimethoxyphenyl)ethyl]-5-fluoro-2-iodo-N—methylbenzenepropanamide | oil |

EXAMPLE 11

2-Iodo-5-methoxy-N,N-dimethylbenzeneethanamine hydrochloride

A solution of 80.8 g (0.253 mole) of 2-iodo-5-methoxy-N,N-dimethylbenzeneacetamide in 800 ml of THF was added over ten minutes of 760 ml of 1M borane in THF. The mixture was heated under reflux for two hours. A 50 ml portion of water was added and the mixture stirred. The solvent was evaporated in vacuo and replaced with 200 ml of propionic acid. The mixture was heated for two hours and poured into ice/sodium hydroxide solution and extracted with ether. The ether solution was washed with sodium hydroxide and water and dried with $K_2CO_3$. The ether was evaporated in vacuo to give 67.3 g of a clear oil which was distilled in a Kugelrohr at 125°–150° C. (0.17 Torr). The distillate was taken up in dilute hydrochloric acid and washed with ether. The aqueous layer was made basic with sodium hydroxide and extracted with ether. The ether solution was dried with $K_2CO_3$ and evaporated in vacuo to give 38.6 g (76% yield) of clear oily 2-iodo-5-methoxy-N,N-dimethylbenzeneethanamine. The hydrochloride was prepared from ether-hydrogen chloride, mp 167.5°–169° C.

EXAMPLE 12

Using the procedure of Example 11 and employing an equivalent quantity of the appropriate amide from Example 10 in place of 2-iodo-5-methoxy-N,N-dimethylbenzeneacetamide the following amines were obtained as products, respectively:

| Product | mp (°C.) |
| --- | --- |
| N—[2-(3,4-Dimethoxyphenyl)ethyl]-2-iodo-5-methoxy-N—methylbenzenepropanamine p-toluensulfonate | 105–106 |
| 2-Iodo-4,5-dimethoxy-N,N—dimethylbenzeneethanamine hydrochloride | 201–203 |
| N—[2-(3,4-Dimethoxyphenyl)ethyl]-2-iodo-N—methyl-5-methylthiobenzenepropanamine oxalate | 132–135 |
| N—[2-(3,4-Dimethoxyphenyl)ethyl]-5-fluoro-2-iodo-N—methylbenzenepropanamine oxalate | 129–131 |
| N—[2-(3,4-Dimethoxyphenyl)ethyl]-6-iodo-N—methyl-1,3-benzodioxole-5-propanamine | oil |
| 2-Iodo-5-methoxy-N,N—dimethylbenzenepropanamine hydrochloride | 168–170 |

EXAMPLE 13

4-(3-Methoxyphenyl)-3-buten-2-one

A solution of 19.08 ml of 10% sodium hydroxide solution was added dropwise to a mixture of 103.6 g (0.761 mole) of 3-methoxybenzaldehyde, 117.2 g (2.02 mole) of acetone and 75 ml of water. The temperature was kept between 24° and 28° by intermittent application of cooling. After 2.75 hours the mixture was acidified with dilute hydrochloric acid and partitioned between $CH_2Cl_2$ and water. The organic layer was washed with water, dried with $MgSO_4$ and concentrated in vacuo to give 132.6 g of a yellow oil. The oil was distilled in a Kugelrohr at 0.5 Torr. A forerun bp 90°–110° C. was taken and discarded. The main fraction was taken between 110° and 120° C. There was obtained 91.68 g (68% yield) of 4-(3-methoxyphenyl)-3-buten-2-one as a yellowish oil.

EXAMPLE 14

1-(3-methoxyphenyl)-1-octen-3-one

Following the procedure of Example 13 and substituting an equivalent quantity of 2-heptanone for acetone there was obtained 1-(3-methoxyphenyl)-1-octen-3-one, bp 110°–134° C., 0.3 mm/Hg.

EXAMPLE 15

4-(3-Methoxyphenyl)-2-butanone

A solution of 30.1 g of 4-(3-methoxyphenyl)-3-buten-2-one in 200 ml of MeOH was hydrogenated over 200 mg of 10% palladium on carbon for two hours. The catalyst was filtered and the solvent evaporated in vacuo to give 30.2 g of yellow oily 4-(3-methoxyphenyl)-2-butanone.

EXAMPLE 16

1-(3-Methoxyphenyl)octan-3-one

Following the procedure of Example 15 and substituting an equivalent quantity of 1-(3-methoxyphenyl)-1-octen-3-one for 4-(3-methoxyphenyl)-3-buten-2-one there was obtained as the product 1-(3-methoxyphenyl)octan-3-one as a colorless oil.

EXAMPLE 17

2-Iodo-5-methoxy-N,N-dimethylalphapentylbenzenepropanamine hydrochloride

A mixture of 13.0 g (0.036 mole) of 1-(2-iodo-5-methoxyphenyl)heptan-2-one, 46.6 ml (0.18 mole) of a solution of 3.86 M dimethylamine in methanol, 8.24 g (0.101 mole) of dimethylamine hydrochloride, 100 ml of methanol and 1.82 g (0.029 mole) of sodium cyanoborohydride was stirred overnight under an atmosphere of nitrogen. Stirring was continued an additional two hours and the reaction mixture acidified to pH 1 by addition of concentrated hyirochloric acid. The solvent was evaporated in vacuo, the residue partitioned between methylene chloride and water, and the methylene chloride layer separated, washed with $Na_2S_2O_5$ solution followed by a washing with 3 M sodium hydroxide solution. The organic phase was dried over anhydrous potassium carbonate and evaporated in vacuo to yield a yellow oil. The oil was dissolved in methanol and the solution treated with ethereal hydrogen chloride to pH 5. The solvent was removed in vacuo and the residue dissolved in 45 ml of refluxing ethyl acetate. Some slight turbidity was removed by filtration through filter aid. The filtrate was cooled to room temperature and diluted with 20 ml of diethyl ether. The solution was cooled overnight in a refrigerator and the resulting solid, 3.34 g, removed by filtration. The filtrate was evaporated in vacuo, the residue triturated with ether and seeded to yield a second crop of off-white solid, 1.66 g. One recrystallization from ethyl acetate yielded pure 2-iodo-5-methoxy-N,N-dimethylalphapentylbenzenepropanamine hydrochloride, mp 100°–103° C.

EXAMPLE 18

N-[2-(3,4-Dimethoxyphenyl)ethyl]-2-iodo-N,alphadimethylbenzeneethanamine Oxalate A solution of 14.5 ml (86.2 mmoles) of homoveratrylamine, 19.0 g (65.5 mmoles) of (2-iodo-5-methoxyphenyl)-2-propanone and 0.162 g (0.86 mmole) of p-toluene sulfonic acid in 250 ml of toluene was heated under reflux with azeotropic removal of water for three hours. The solvent was evaporated in vacuo to give 34.7 g of the corresponding imine as an oil.

The imine was dissolved in 250 ml of MeOH and 3.5 g (55.2 mmoles) of sodium cyanoborohydride was added. The mixture was stirred for 18 hours. Hydrogen chloride gas was admitted slowly to lower the pH to below one. The residue was partitioned between ether and aqueous NaOH solution. The ether layer was washed with brine and dried ($K_2CO_3$). Carbon dioxide was passed through the solution over one hour. The precipitated homoveratrylamine carbonate was removed by filtration. The filtrate was evaporated to dryness in vacuo.

The residue, 29.9 g (65.7 mmoles) of crude N-[2-(3,4-dimethoxyphenyl)ethyl]-2-iodo-5-methoxyalphamethylbenzeneethanamine, was taken up in 300 ml of MeOH and 10 ml (0.131 mole) of formalin and 5.0 g (78.8 mmoles) of sodium cyanoborohydride were added. The mixture was stirred for 22 hours.

Methanolic hydrogen chloride was added to bring the pH to one. The solvent was evaporated in vacuo. The residue was partitioned between ether and aqueous NaOH solution. The ether was dried ($K_2CO_3$) and the solvent evaporated in vacuo to give 30.2 g of a colorless oil.

An oxalate salt was prepared in 95% ethanol to give N-[2-(3,4-dimethoxyphenyl)ethyl]-2-iodo-5-methoxy-N,alphadimethylbenzeneethanamine oxalate as a white crystalline solid, mp 178°–179° C.

EXAMPLE 19

2-(1-Hexynyl)-5-methoxy-N,N-dimethylbenzeneethanamine hydrochloride (1:1)

A solution of 2.7 ml (0.027 mole) 1-hexyne in 10 ml dry (4 A sieves) tetrahydrofuran was cooled to 0° C. in an ice bath. Argon was passed over the solution 10.4 ml (0.027 mole) 2.69 M n-BuLi was added slowly via syringe through a serum cap. The resulting solution was stirred 20 minutes under argon. During this time, a second flask containing 3.2 g (0.027 mole) anhydrous zinc chloride was attached to the first flask via cannula. After the 20 minutes the contents of the first flask was transferred to the second flask via cannula. The second flask was cooled to 0° C. This solution was stirred for 20 minutes, then 5 g (0.016 mole) 2-iodo-5-methoxy-N,N-dimethylbenzeneethanamine in 20 ml dry tetrahydrofuran was added via syringe. 0.32 g (mole 1%) tetrakis(triphenylphosphine) palladium was added to the reaction mixture which was stirred overnight at room temperature under nitrogen. Water was added to the reaction mixture and the organics were evaporated in vacuo. The residue was taken up in methanol, the solid catalyst was filtered off and the methanol was evaporated in vacuo. Methylene chloride was added to the aqueous residue, the organic layer was washed with sodium bicarbonate solution, water, brine solution and dried over potassium carbonate. The organics were evaporated in vacuo to give a red oil. Addition of ethereal hydrogen chloride gave white crystals which upon recrystallization from acetonitrile gave 1.27 g (27% yield) of 2-(1-hexynyl)-5-methoxy-N,N-dimethylbenzeneethanamine hydrochloride, mp 145.5°–147.5° C.

EXAMPLE 20

Following the procedure of Example 19 and employing an equivalent quantity of the appropriate iodoarylalkaneamine in place of 2-iodo-5-methoxy-N,N-dimethylbenzeneethanamine and the appropriate 1-alkyne in place of 1-hexyne there were obtained as products, respectively:

| Product | mp (°C.) |
|---|---|
| 2-(Cyclohexylethynyl)-3,4-dimethoxy-N,N—dimethyl-benzeneethanamine (E)-2-Butenedioate (1:1) | 162–163 |
| 2-(1-Hexynyl)-5-methoxy-N,N—dimethylbenzene-propanamine Cyclohexylsulfamate (1:2) | 139–140 |
| N—[2-(3,4-Dimethoxyphenyl)ethyl]-6-(1-hexynyl)-N—methyl-1,3-benzodioxole-5-propanamine | oil |
| 2-(1-Decynyl)-5-methoxy-N,N—dimethylbenzene-propanamine 2-Naphthalenesulfonate hydrate (10:10:11) | 68–70 |
| 2-(3,3-Dimethylbutynyl)-5-methoxy-N,N—dimethyl-benzenepropanamine Cyclohexylsulfamate (1:2) | 146–148 |
| N—[2-(3,4-Dimethoxyphenyl)ethyl]-2-(1-hexynyl)-5-methoxy-N—methylbenzenepropanamine Cyclohexyl-sulfamate Hydrate (2:4:1) | 107–110 |
| N—[2-(3,4-Dimethoxyphenyl)ethyl]-2-(3,3-dimethyl-butynyl)-5-methoxy-N—methylbenzenepropanamine Cyclohexylsulfamate (1:2) | 117–119 |
| N—[2-(3,4-Dimethoxyphenyl)ethyl]-5-methoxy-N—methyl-2-(4-phenyl-1-butynyl)benzenepropanamine Cyclohexylsulfamate (1:2) | 109–111 |
| 2-[3-(Diethylamino)-1-propynyl]-N—[2-(3,4-dimethoxyphenyl)ethyl]-5-methoxy-N—methyl-benzenepropanamine Hydrochloride (1:2) | 171–173 |
| 2-(Butynyl)-N—[2-(3,4-dimethoxyphenyl)ethyl]-5-methoxy-N—methylbenzenepropanamine Cyclohexyl-sulfamate (1:2) | 114–117 |
| 2-(Cyclohexylethynyl)-N—[2-(3,4-dimethoxyphenyl)-ethyl]-5-methoxy-N—methylbenzenepropanamine Cyclohexylsulfamate (1:2) | 115–117 |

EXAMPLE 21

2-(1-Hexynyl)-5-methoxy-N,N-dimethylalphapentyl-benzenepropanamine (E)-2-butendioate A solution of 4.59 g (11.8 mmoles) of 2-iodo-5-methoxy-N,N-dimethylalphapentylbenzenepropanamine in 22 ml of triethylamine was treated with 1.76 ml (15.3 mmoles) of 1-hexyne. 0.022 g (0.12 mmole) of copper (I) iodide and 0.041 g (0.06 mmole) of (Ph$_3$P)$_2$Pd(II)Cl$_2$. The mixture was stirred for three days at room temperature. The reaction mixture was treated with 150 ml of water and extracted with ether. The ether phase was washed four times with water and once with brine, dried (K$_2$CO$_3$) and evaporated in vacuo to give 3.72 g of an oil. A fumarate salt was prepared in MeOH solvent. There was obtained 3.35 g of cyrstalline product in three crops. Recrystallization from acetonitrile-ether afforded 3.07 g (57% yield) of crystalline 2-(1-hexynyl)-5-methoxy-N,N-dimethylalphapentyl-benzenepropanamine (E)-2-butenedioate (2:3), mp 125°–126° C.

Elemental Analysis: Calculated for C$_{23}$H$_{37}$NO.1.5 C$_4$H$_4$O$_4$: C, 67.29; H, 8.37; N, 2.70 Found: C, 67.21; H, 8.41; N, 2.70.

EXAMPLE 22

Following the procedure of Example 21 and substituting an equivalent quantity of N-[2-(3,4-dimethoxyphenyl)ethyl]-2-iodo-5-methoxy-N,alpha-dimethylbenzeneethanamine for 2-iodo-5-methoxy-N,N-dimethylalphapentylbenzenepropanamine and an equivalent quantity of the appropriate acetylene for 1-hexyne there were obtained as products (oils), respectively:

2-(Cyclohexylethynyl)-N-[2-(3,4-dimethoxyphenyl)ethyl]-5-methoxy-N,alphadimethylbenzeneethanamine $^1$H NMR (CDCl$_3$): 7.24–7.20 (m, 1H); 6.78–6.62 (m, 5H); 3.85 (s, 3H); 3.83 (s, 3H); 3.75 (s, 3H); 2.71–2.65 (m, 5H); 2.50 (m, 1H); 2.39 (s, 3H); 1.82–1.68 (m, 4H); 1.46–1.27 (m, 6H) 0.94 (d, J=7.2 Hz, 3H).

N-[2-(3,4-Dimethoxyphenyl)ethyl]-2-(1-hexynyl)-5-methoxy-N,alphadimethylbenzeneethanamine $^1$H NMR (CDCl$_3$) 7.30–7.25 (m, 1H); 6.76–6.66 (m, 5H); 3.86 (s, 3H); 3.84 (s, 3H); 3.76 (s, 3H); 3.18–3.02 (m, 3H); 2.75 (s, 4H); 2.62–2.55 (m, 1H); 2.39 (s, 3H); 2.31 (t, J=7 Hz, 2H); 1.58–1.37 (m, 4H); 0.95 (d, J=7 Hz, 3H); 0.87 (t, J=7 Hz, 3H).

EXAMPLE 23

N-[2-(3,4-Dimethoxyphenyl)ethyl]-2-(3-hydroxy-3-methylbutynyl)-5-methoxy-N-methylbenzenepropanamine (E)-2-butenedioate (2:1)

A solution of 5.0 g (10.7 mmoles) of N-[2-(3,4-dimethoxyphenyl)ethyl]-2-iodo-5-methoxy-N-methylbenzenepropanamine in 100 ml of triethylamine was treated with 1.3 ml of 2-methyl-3-butyn-2-ol, 214 mg of Pd ($\phi_3$P)$_2$Cl$_2$ and 107 mg Copper (I) iodide. The mixture was stirred overnight and the triethylamine removed in vacuo. The residue was dissolved in diethyl ether and the insoluble solids removed by filtration. The filtrate was washed sequentially with water, sodium bicarbonate solution, water, and brine. The ether layer was dried over anhydrous potassium carbonate and the solvent removed in vacuo to yield 9.5 g of a brown liquid. The brown liquid was treated under additional vacuum to remove all triethylamine and the residue treated with one-half equivalent of fumaric acid in methanol and isopropanol to yield a crude fumarate salt. The crude salt was recrystallized from methanol/isopropanol to yield 6.69 g of pure N-[2-(3,4-dimethoxyphenyl)ethyl]-2-(3-hydroxy-3-methylbutynyl)-5-methoxybenzenepropanamine (E)-2-butenedioate (2:1), mp 160°–161° C.

Elemental Analysis: Calculated for C$_{26}$H$_{35}$NO$_4$.½ C$_4$H$_4$O$_4$: C, 69.54; H, 7.71; N, 2.90 Found: C, 69.51; H, 7.75; N, 2.87.

EXAMPLE 24

N-[2-(3,4-Dimethoxyphenyl)ethyl]-2-ethynyl-5-methoxy-N-methylbenzenepropanamine Cyclohexylsulfamate (1:2)

A solution of 4.6 g (0.01 mole) of N-[2-(3,4-dimethoxyphenyl)ethyl]-2-(3-hydroxy-3-methylbutynyl)-5-methoxy-N-methylbenzenepropanamine in 150 ml of toluene when treated with 1 ml of 50% aqueous NaOH solution and 0.3 g of tetra-n-butylammonium choloride.

The mixture was heated under reflux for 16 hours. An additional 0.6 g of tetra-n-butylammonium chloride was added and refluxing was continued for four hours. An additional 0.6 g of tetra-n-butylammonium chloride was added and refluxing was continued for 20 hours. The solvent was evaporated in vacuo and the residue partitioned between ether and water. The organic phase was washed with water and brine, dried ($K_2CO_3$) and the solvent evaporated in vacuo to give 5.2 g of a brown oil. The oxalate salt was prepared and recrystallized from 95% ethanol. The oxalate was reconverted to the base by partitioning between ether and NaOH solution. The resulting ether solution was evaporated and the residue flash chromatographed on silica gel using a mixture of one part MeOH to 20 parts $CHCl_3$ as the eluant. The fraction containing the desired amine was evaporated in vacuo. The residue was dissolved in 2-propanol and treated with two equivalents of cyclohexylsulfamic acid. There was obtained 0.61 g of N-[2-(3,4-dimethoxyphenyl)ethyl]-2-ethynyl-5-methoxy-N-methylbenzenepropanamine cyclohexylsulfamate (1:2) as a crystalline solid, mp 120°–122° C.

Elemental Analysis: Calculated for $C_{23}H_{29}NO_3.2 C_6H_{13}NO_3S$: C, 57.91; H, 7.64; N, 5.79 Found: C, 57.55; N, 7.72; N, 5.74.

EXAMPLE 25

Ethyl 3-aminobenzenepropanoate hydrochloride

A suspension of 100 g (0.52 moles) of 3-nitrocinnamic acid in 800 ml glacial acetic acid and 100 ml of methanol was hydrogenated at 50 pounds per square inch over 2.5 g 10% palladium on carbon until four equivalents of hydrogen were absorbed. The catalyst was filtered off, the filtrates combined and the solvent was concentrated in vacuo leaving a brown glass of 3-aminobenzenepropanoic acid. To this was added 1 liter of ethanolic hydrochloric acid which was brought to reflux for five hours. The solvent was evaporated off in vacuo leaving a purple solid. Recrystallization from ethyl acetate yielded 88.0 g of ethyl 3-aminobenzenepropanoate hydrochloride, mp 132°–135° C., (74% yield).

EXAMPLE 26

Ethyl 5-amino-2-iodobenzenepropanoate hydrochloride

To a solution of 88.0 g (0.38 moles) ethyl 3-aminobenzenepropanoate in 380 ml glacial acetic acid was added 97.3 g (0.38 moles) iodine and 96.0 g (0.57 moles) silver acetate portionwise, alternating the additions beginning with the iodine. After two hours of stirring 10 g of iodine was added and stirring was continued for an additional hour. The reaction mixture was filtered and the solid washed well with acetic acid. The filtrate was extracted with chloroform. The chloroform layer was washed with sodium bisulfite solution then evaporated in vacuo. The resulting red oil was converted to the hydrochloric acid salt giving 118.3 g of ethyl 5-amino-2-iodobenzenepropanoate hydrochloride, mp 124°–127° C. (72% yield).

EXAMPLE 27

Sodium 2-iodo-5-methylthiobenzenepropanoate

A mixture of 30 g (0.089 moles) of ethyl 5-amino-2-iodobenzenepropanoate, 30 ml water, 20 g ice and 45 ml of hydrochloric acid was stirred for one hour. The solution was cooled to 0° C. and 5.8 g (0.084 moles) of sodium nitrite in 15 ml of water were added dropwise keeping the temperature below 5° C. After stirring for one hour the reaction mixture was added to a solution of 13.5 g (0.084 moles) of potassium ethyl xanthate in 20 ml of water. This was stirred for three hours. The reaction mixture was extracted several times with diethyl ether which was evaporated in vacuo. The resulting brown oil was taken up in 95% ethanol and 18.9 g (0.336 moles) of potassium hydroxide was added. After refluxing overnight under nitrogen the reaction was cooled. Methyl iodide (10.5 ml; 0.168 moles) was added and the reaction was stirred three more hours. The ethanol was evaporated in vacuo. The residue was partitioned between 3 N hydrochloric acid and diethyl ether. The ether was washed with water, brine solution and dried over $MgSO_4$. The ether was evaporated off. Conversion to the sodium salt gave 14.3 g of sodium 2-iodo-5-methylthiobenzenepropanoate, mp 118°–122° C. (49% yield).

EXAMPLE 28

3-(5-Fluoro-2-iodophenyl)propionic acid

A mixture of 30 g (0.084 mole) of ethyl 3-(5-amino-2-iodophenyl) propanoate 45 ml of concentrated hydrochloric acid, 25 ml of water, and 40 g of ice was stirred for 40 minutes then cooled to −10° C. A solution of 5.8 g of sodium nitrite in 20 ml of water was added dropwise with stirring while maintaining a temperature of −10° C. Stirring was continued for 1½ hours then 13 ml of 65% hexafluorophosphoric acid was added slowly and the mixture allowed to warm to room temperature and stirring for a period of one hour. The resulting solid was removed by filtration and washed with water, 1:4::ethanol:water, and finally water. The solid was dried in vacuo, placed in 500 ml of xylene and heated at 130° for 2.5 hours, until gas evolution ceased. The solvent was removed in vacuo and the residue partially dissolved in ether. The insolubles were removed by filtration and the filtrate washed with sodium bicarbonate solution, 3 N hydrochloric acid, water, and brine. The solvent was removed in vacuo to yield a brown oil which was purified by flash chromatography on silica using mixtures of ethyl acetate and hexane as the eluting solvent. The eluate was stripped in vacuo, the residue dissolved in ether, insolubles removed by filtration, and finally the solvent removed in vacuo to yield 9.3 g of nearly pure fluoro-iodo ester, a yellow oil.

The ester was dissolved in 100 ml of methanol and treated with 15.5 ml of 3 N sodium hydroxide solution. The mixture was refluxed for three hours and the solvent removed in vacuo. The resulting residue was poured into 3 N hydrochloric acid while cooling by addition of ice. The aqueous mixture was extracted with ether, the ether washed with brine and dried over anhydrous magnesium sulfate. The solvent was removed in vacuo to yield 8.9 g of 3-(5-fluoro-2-iodophenyl)propionic acid, a yellow oil.

EXAMPLE 29

Starting with 1-(3-methoxyphenyl)octanone from Example 16 and employing the procedures of Examples 18 and 21 there was obtained as the product N-[2-(3,4-dimethoxyphenyl)-ethyl]-2-(1-hexynyl)-5-methoxy-N-methyl-α-pentyl-benzenepropanamine ethanedioate (1:1), mp 102°–104° C.

What is claimed is:

1. An acetylene of the following formula (I):

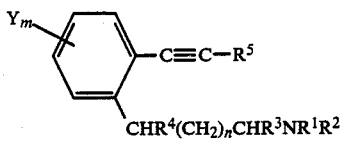

wherein
Y is independently alkyl, alkoxy, alkylthio, alkylsulfinyl, alkylsulfonyl, alkanoyloxy, alkanoylamino, amino, monoalkylamino, dialkylamino, hydroxy, halogen or cyano and m is 0, 1 or 2 or Y is methylenedioxy or ethylenedioxy at adjacent ring carbons and m is 2;

$R^1$ and $R^2$ are independently hydrogen, alkyl or

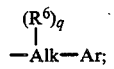

$R^3$ is hydrogen, alkyl or alkoxyalkyl;
n is 0, 1 or 2;
$R^4$ is hydrogen or alkyl;
$R^5$ is hydrogen, alkyl, cycloalkyl or alkyl substituted by amino, monoalkylamino, dialkylamino, hydroxy, cycloalkyl or alkoxy;
Alk is a straight chain alkylene of about 1 to 4 carbons;
Ar is a phenyl, phenoxy, thiophenoxy or a furan, thiophene, pyrrole or pyridine ring which rings may be substituted independently by one or more of alkyl, alkoxy, alkylthio, hydroxy, halogen, fluoroalkyl, amino or dialkylamino or by methylenedioxy at adjacent ring carbons;
$R^6$ is alkyl; and
q is 0, 1 or 2 if Alk is alkylene of 1 carbon or q is 0, 1, 2 or 3 if Alk is alkylene of about 2 to 4 carbons,
and the pharmaceutically acceptable acid addition salts and quaternary ammonium compounds with an alkylhalide or alkylsulfate thereof.

2. The acetylene of claim 1, wherein
Y is alkyl of about 1 to 6 carbons; alkoxy of about 1 to 6 carbons; alkylthio of about 1 to 6 carbons; alkylsulfinyl of about 1 to 6 carbons; alkylsulfonyl of about 1 to 6 carbons; alkanoyloxy of about 2 to 6 carbons; alkanoylamino of about 2 to 6 carbons; amino; monoalkylamino of about 1 to 6 carbons; dialkylamino of about 2 to 12 carbons; hydroxy; fluoro, chloro or bromo; cyano; or methylenedioxy or ethylenedioxy;

$R^1$ and $R^2$ are independently hydrogen, alkyl of about 1 to 8 carbons or

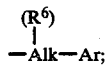

$R^3$ is hydrogen, alkyl of about 1 to 6 carbons or alkoxyalkyl of about 1 to 6 carbons in each alkyl portion;
n is 0, 1 or 2;
$R^4$ is hydrogen or alkyl of about 1 to 6 carbons;
$R^5$ is hydrogen, alkyl of about 1 to 12 carbons, cycloalkyl of about 5 to 7 carbons or alkyl of about 1 to 6 carbons substituted by amino, monoalkylamino of about 1 to 6 carbons, dialkylamino of about 2 to 6 carbons, hydroxy, cycloalkyl of about 5 to 7 carbons or alkoxy of about 1 to 6 carbons;
Alk is methylene, ethylene, trimethylene or tetramethylene;
Ar is phenyl, phenoxy, thiophenoxy or a furan, thiophene, pyrrole or pyridine ring which rings may be substituted by one or more of alkyl, alkoxy or alkylthio of about 1 to 6 carbons each, hydroxy, fluoro, chloro, bromo, fluoroalkyl of about 1 to 6 carbons, amino, dialkylamino of about 2 to 12 carbons or methylene dioxy;
$R^6$ is alkyl of about 1 to 4 carbons; and
q is 0, 1 or 2,
and the pharmaceutically acceptable acid addition salts and quaternary ammonium compounds with an alkylhalide or alkylsulfate thereof.

3. The acetylene of claim 1, wherein said Ar is a pyridine ring.

4. The acetylene of claim 1, wherein said pharmaceutically acceptable acid addition salts are formed from acids selected from the group consisting of hydrochloric, hydrobromic, hydroiodic, sulfuric, phosphoric, fumaric, maleic, cyclohexylsulfamic, citric, lactic and methanesulfonic and said quaternary ammonium compounds are those formed with an alkylhalide or alkylsulfate.

5. The acetylene of claim 1, wherein Y is alkoxy and m is 1 or 2.

6. The acetylene of claim 1, wherein Y is alkoxy and m is 1 at the position para to acetylene moiety or Y is alkoxy and m is 2 at positions para to the acetylene moiety and to the $-CHR^4(CH_2)_nCHR^3NR^1R^2$ moiety.

7. The acetylene of claim 1, wherein one of $R^1$ and $R^2$ is hydrogen or alkyl.

8. The acetylene of claim 1, wherein $R^1$ and $R^2$ are both alkyl or $R^1$ is alkyl and $R^2$ is 2-(3,4-dimethoxyphenyl)-ethyl.

9. The acetylene of claim 1, wherein $R^5$ is hydrogen, alkyl, cycloalkyl or alkyl substituted by dialkylamino or hydroxy.

10. The acetylene of claim 1 wherein
$R^1$ is alkyl and $R^2$ is $CH_2CH_2Ar$.

11. The acetylene of claim 1, wherein Y is alkoxy, alkylthio, amino, halogen or methylenedioxy at adjacent ring carbons; m is 0, 1 or 2; $R^1$ and $R^2$ are independently alkyl or $-CH_2CH_2Ar$;
$R^3$ is hydrogen or alkyl; n is 0 or 1; $R^4$ is hydrogen;
$R^5$ is hydrogen, alkyl, cycloalkyl or alkyl substituted by dialkylamino or hydroxy; and Ar is phenyl substituted by one or more alkoxy groups.

12. The acetylene of claim 1, wherein said acetylene is selected from the group consisting of:
2-(1-hexynyl)-5-methoxy-N,N-dimethylbenzeneethanamine;
2-(cyclohexylethynyl)-3,4-dimethoxy-N,N-dimethylbenzeneethanamine;
2-(1-hexynyl)-5-methoxy-N,N-dimethylbenzenepropanamine;
N-[2-(3,4-dimethoxyphenyl)ethyl]-6-(1-hexynyl)-N-methyl-1,3-benzodioxole-5-propanamine;
2-(1-decynyl)-5-methoxy-N,N-dimethylbenzenepropanamine;
2-(3,3-dimethylbutynyl)-5-methoxy-N,N-dimethylbenzene propanamine;
N-[2-(3,4-dimethoxyphenyl)ethyl]-2-(1-hexynyl)-5-methoxy-N-methylbenzenepropanamine;

N-[2-(3,4-dimethoxyphenyl)ethyl]-2-(3,3-dimethylbutynyl)-5-methoxy-N-methylbenzenepropanamine;

2-[3-(diethylamine)-1-propynyl]-N-[2-(3,4-dimethoxyphenyl)ethyl]-5-methoxy-N-methylbenzenepropanamine;

2-(butynyl)-N-[2-(3,4-dimethoxyphenyl)ethyl]-5-methoxy-N-methylbenzenepropanamine;

2-(cyclohexylethynyl)-N-[2-(3,4-dimethoxyphenyl)ethyl]-5-methoxy-N-methylbenzenepropanamine;

2-(1-hexynyl)-5-methoxy-N,N-dimethyl-alpha-pentylbenzenepropanamine;

2-(cyclohexylethynyl)-N-[2-(3,4-dimethoxyphenyl)ethyl]-5-methoxy-N,alpha-dimethylbenzeneethanamine;

N-[2-(3,4-dimethoxyphenyl)ethyl]-2-(1-hexynyl)-5-methoxy-N,alpha-dimethylbenzeneethanamine;

N-[2-(3,4-dimethoxyphenyl)ethyl]-2-(3-hydroxy-3-methylbutynyl)-5-methoxy-N-methylbenzenepropanamine;

N-[2-(3,4-dimethoxyphenyl)ethyl]-2-ethynyl-5-methoxy-N-methylbenzene-propanamine; and N-[2-(3,4-dimethoxyphenyl)ethyl]-2-(1-hexynyl)-5-methoxy-N-methyl-α-pentyl-benzenepropanamine, and the pharmaceutically acceptable acid-addition salts and quaternary ammonium compounds thereof.

13. The acetylene of claim 1, wherein $R^5$ is cycloalkyl.

14. The acetylene of claim 1, wherein $R^5$ is alkyl.

15. The acetylene of claim 1, wherein $R^5$ is n-butyl.

16. A pharmaceutical composition for the treatment of hypertension or angina pectoris comprising an anti-hypertensively or anti-anginally effective amount of an acetylene of claim 1 in combustion with a pharmaceutically acceptable diluent or carrier.

17. A method for treating hypertension or angina pectoris which comprises administering to a mammal in need thereof, the pharmaceutical composition of claim 16.

* * * * *